(12) United States Patent
Nguyen

(10) Patent No.: US 8,939,990 B2
(45) Date of Patent: Jan. 27, 2015

(54) BIRTHING GLOVE

(76) Inventor: Bich Van Nguyen, Silver Spring, MD (US)

( * ) Notice: Subject to any disclaimer, the term of this patent is extended or adjusted under 35 U.S.C. 154(b) by 698 days.

(21) Appl. No.: 13/046,002

(22) Filed: Mar. 11, 2011

(65) Prior Publication Data
US 2011/0230892 A1    Sep. 22, 2011

Related U.S. Application Data

(60) Division of application No. 10/910,313, filed on Aug. 4, 2004, now abandoned, which is a continuation-in-part of application No. 10/196,255, filed on Jul. 17, 2002, now abandoned.

(51) Int. Cl.
| | |
|---|---|
| *A61B 17/42* | (2006.01) |
| *A61B 17/44* | (2006.01) |
| *A61B 19/04* | (2006.01) |
| *A61B 17/00* | (2006.01) |

(52) U.S. Cl.
CPC ............... *A61B 17/42* (2013.01); *A61B 17/44* (2013.01); *A61B 17/442* (2013.01); *A61B 19/04* (2013.01); *A61B 2017/00557* (2013.01)
USPC .......................................... 606/122

(58) Field of Classification Search
USPC ........... 606/122, 121, 119; 2/158, 159, 161.6, 2/161.7
See application file for complete search history.

(56) References Cited

U.S. PATENT DOCUMENTS 6,485,467 B1 *  11/2002  Crook et al. .................. 604/174

* cited by examiner

*Primary Examiner* — Kathleen Holwerda
*Assistant Examiner* — Sarah Simpson
(74) *Attorney, Agent, or Firm* — Millen, White, Zelano & Branigan, P.C.

(57) ABSTRACT

A birthing glove exposes portions of the finger and thumb, which may be covered by a regular surgical glove. The birthing glove has a trank having an inner wall covering the palm and backhand of the birthing practitioner. Four finger sleeves and a thumb sleeve extend from the trank and terminate over the first phalanx of each finger. A cuff extends from the trank for covering at least a portion of the practitioner's forearm and an inflatable bladder is disposed over the inner wall of the trank adjacent to the back of the hand for inflation in order to expand behind the exposed fingers and thumb of the practitioner in order to dilate the birth canal and provide access to the head of the infant.

14 Claims, 5 Drawing Sheets

BIRTHING GLOVE

RELATED APPLICATION

The present invention is a divisional of U.S. application Ser. No. 10/910,313, filed May 17, 2010, now abandoned which is a continuation-in-part of U.S. application Ser. No. 10/196,255, filed Jul. 17, 2002 which is now abandoned; all of which are hereby incorporated by reference.

FIELD OF THE INVENTION

The present invention relates to birthing gloves. More particularly, the present invention relates to a birthing gloves which facilitate passage of an infant through a birthing canal.

BACKGROUND OF THE INVENTION

A current practice by obstetricians is to utilize obstetric forceps for grasping a baby's head during childbirth. Generally, obstetric forceps have metal elements which are used to grasp a baby's head and assist in the birth by pulling on the forceps to extract the infant through the birth canal and out of the mother's body.

With obstetric forceps there is a risk of injury to a baby's head, the injury ranging from nerve damage to impression fractures of the skull caused by excessive pressure applied by the forceps to the infants head during delivery. The pressure on an infant's head is not adequately controllable because the obstetrician must rely on finger sensitivity which is displaced from the baby by the length of the forceps. If the obstetrician is strong or inexperienced excess forceps pressure may occur.

Moreover, obstetric forceps have a particular shape whereas baby's heads have different shapes so that situations arise where pressure is applied at inappropriate locations on the infant's head at excessive levels. Clearly, forceps tend to isolate from an obstetrician or other birthing practitioner from the infant being delivered.

In view of these considerations there is a need for an approach to birth canal obstetrics which does not rely on forceps.

SUMMARY OF THE INVENTION

A birthing glove exposing portions of the fingers and the thumb of a birthing practitioner, comprises a trank having an inner wall covering the palm and back of a hand of the practitioner and four finger sleeves and a thumb sleeve extending from the trank. The sleeves have open ends that terminate in front of the third phalanx of each finger and the second phalanx of the thumb of the practitioner. A cuff extends from the trank for covering at least a portion of the practitioner's arm and a bladder is disposed at least over the inner wall of the trank adjacent to the back of the metacarpals and carpals of the hand for inflation to expand behind the fingers and thumb of the practitioner so as to widen the birth canal.

In a first aspect of the birthing glove the open ends of the finger and thumb sleeves terminate in seals.

In still a further aspect of the invention, the sleeves have a length which extends over only a portion of the first phalanges of the fingers and the thumb.

In still a further aspect of the birthing glove, a bladder extends only over the back side of the metacarpal with no sufficient over the palm of the hand to allow flexibility of the metacarpus when the hand is inserted through the birth canal.

In a further aspect of the invention the birthing glove is used in combination with a thin close fitting surgical glove which covers the entire hand including all of the fingers and thumb of the practitioner to hygienically isolate the practitioners hand from the infant and mother.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
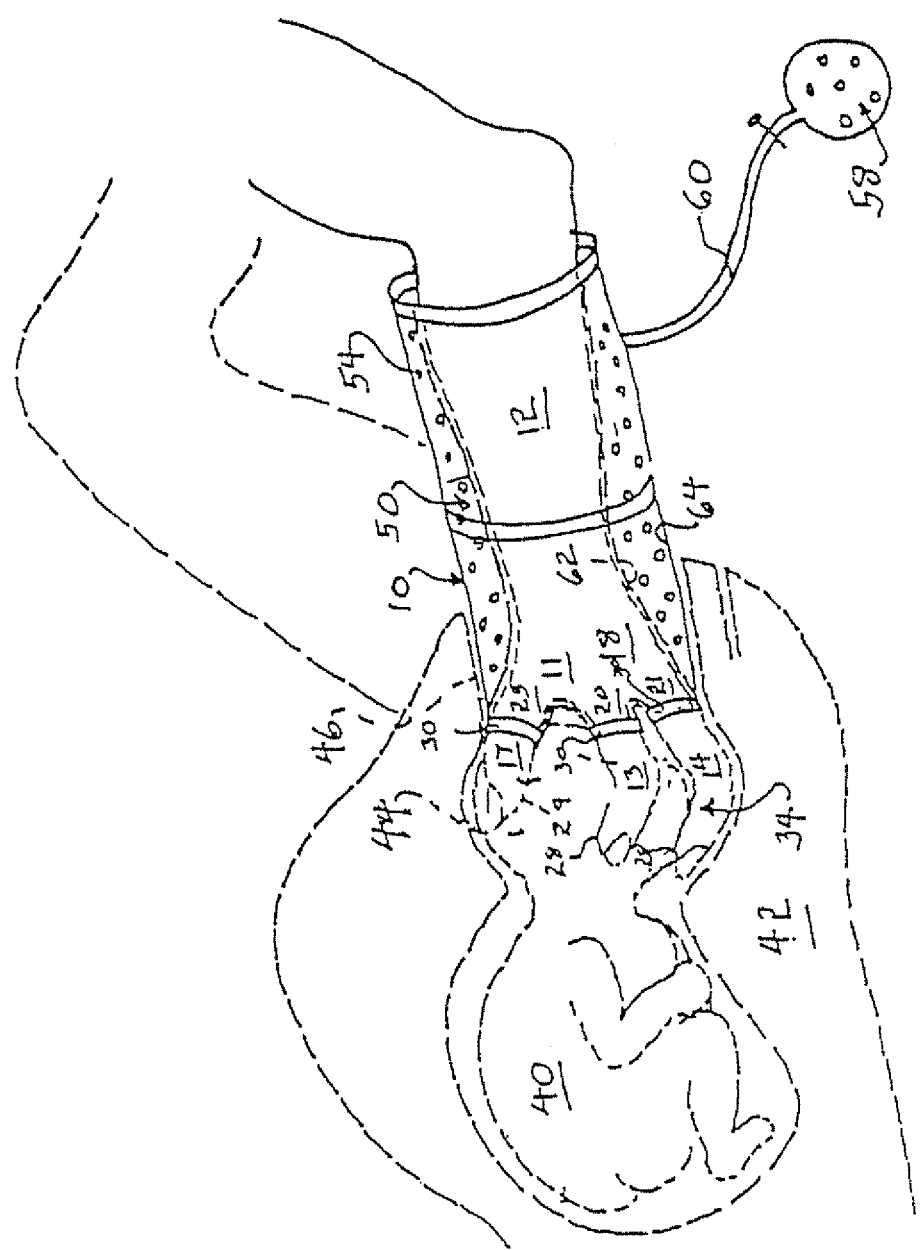
FIG. 1 is a perspective view of an infant being grasped by a birthing practitioner's hand extended through the birth canal utilizing the birthing glove of the present invention.
Figure 2:
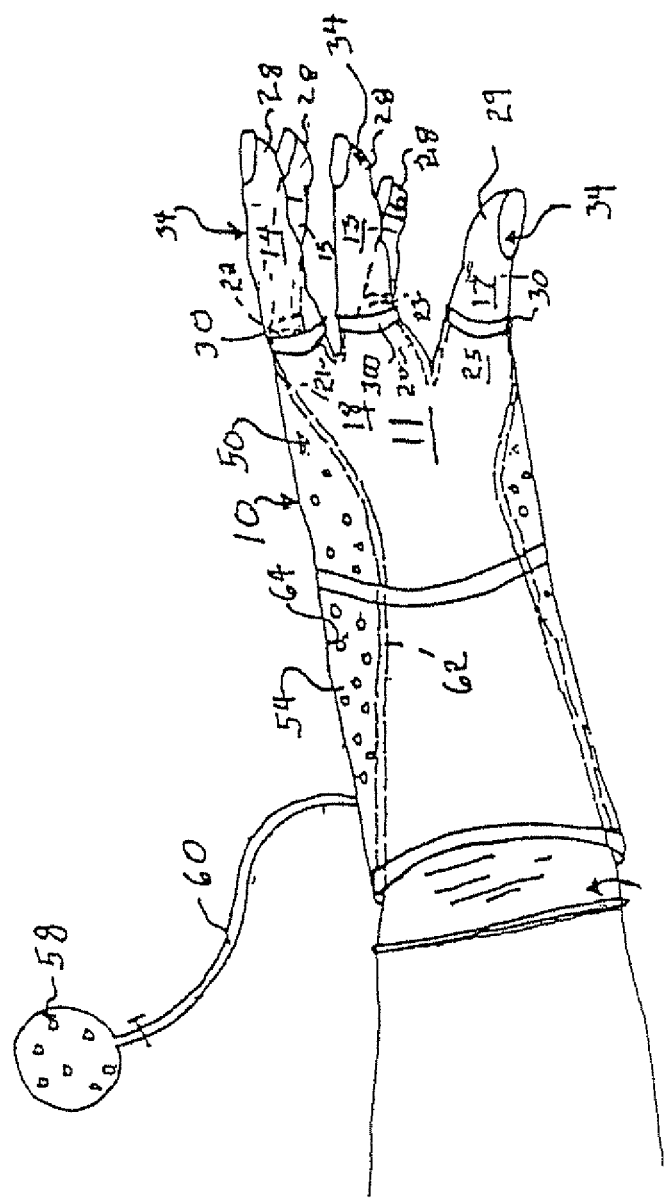
FIG. 2 is a side view partially in elevation of the birthing glove shown in FIG. 1.

Referring now to FIGS. 1 and 2 there is shown a birthing glove 10 configured in accordance with the principles of the present invention. The birthing glove 10 covers the hand 11 and a substantial portion of a forearm 12 of a birthing practitioner who may be an obstetrician or midwife.

Figure 3:
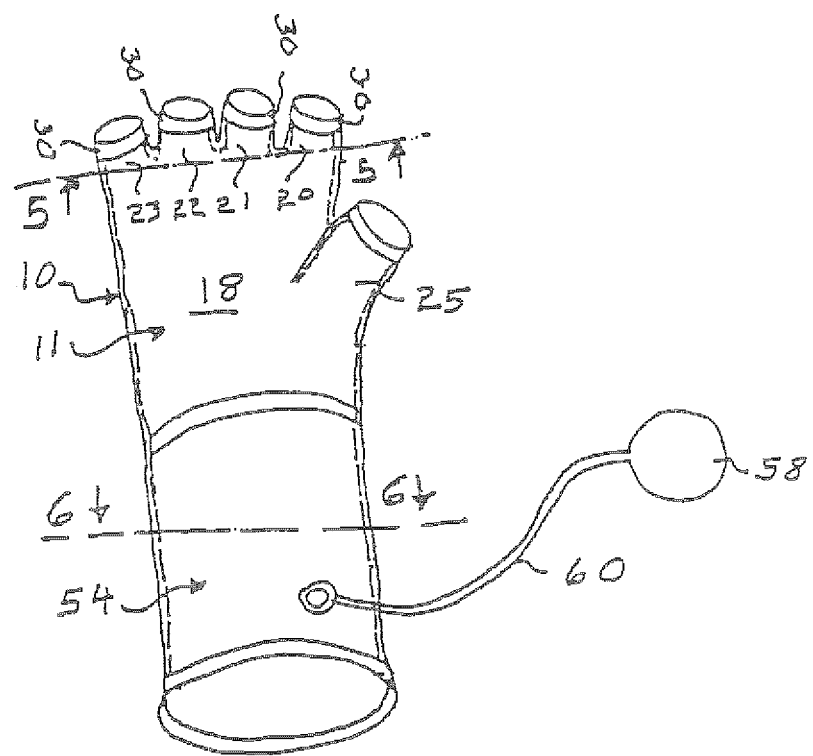
FIG. 3 is a front view of the birthing glove of FIGS. 1 and 2.
Figure 4:
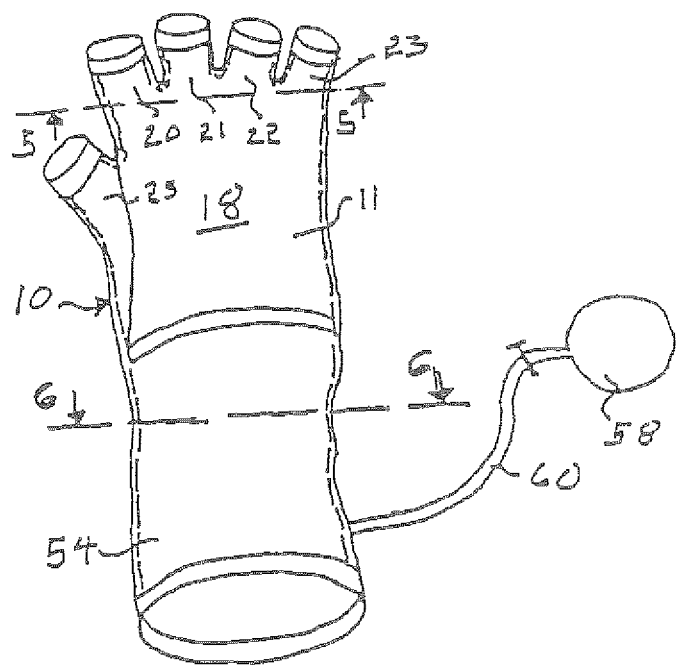
FIG. 4 is a back view of the birthing glove of FIGS. 1-3.

As is evident in FIGS. 1 and 2 the four fingers 13, 14, 15 and 16 as well as the thumb 17 of the practitioners hand 11 are partially covered by sleeves 20, 21, 22, 23 and 25, respectively, leaving at least the fingertips 28 and thumb tip 29 uncovered by the birthing glove 10. Preferably, the open-ended sleeves 20-24 extend over only the first phalange (bone) of each of the fingers 13-16 and the thumb 17. Each of the open-ended sleeves 20-24 has an annular seal 30 thereon to seal against the fingers 13-16 and thumb 17 (see also FIGS. 3 and 4).

Preferably, the hand 11 of the birthing practitioner is completely enclosed by a relatively thin surgical glove 34 that completely encloses each of the fingers 11-16 and the thumb 17 so as to provide a hygienic relationship with respect to the infant 40 (FIG. 1) and the mother 42 (FIG. 1). By having only a thinned surgical glove 34, the patients hand 11 is able to provide the practitioner with feel or tactile sense with respect to the head 44 of the infant 40. Moreover, this tactile sense enables the practitioner to control the amount of pressure applied by the hand 11 against the infant's head 44 and to detect just where on the infant's head finger and hand pressure is being applied.

As is apparent in FIG. 1, the birth canal 46 through which the practitioners' hand 11 extends has been widened by a bladder 50 which is integral with the trank 18 of the glove which covers the palm of the hand 11 and the back surface of the hand. The bladder 50 preferably extends back through a cuff portion 54 of the birthing glove 10 and surrounds a substantial portion of the birthing practitioners forearm 12. The bladder is connected to a source of air pressure 58 via a flexible tube 60. The force of air pressure 58 is preferably controlled by the practitioner's other hand in conjunction with visual observations by the birthing practitioner of the mother, medical monitors and tactual information from the practitioners' fingers 13-16 and thumb 17 as well as the practitioners' palm.

Figure 5:
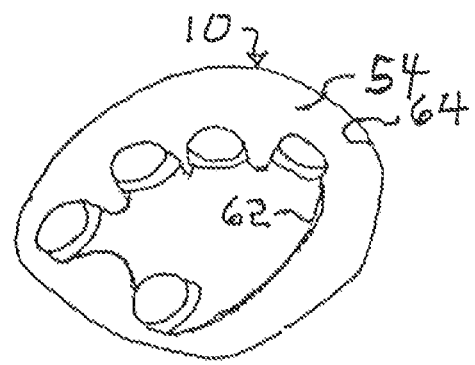
FIG. 5 is an elevation through the birthing glove taken along lines 5-5 of FIGS. 3 and 4.
Figure 6:
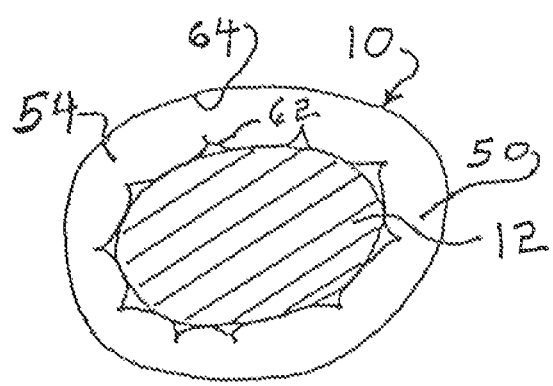
FIG. 6 is an elevational view taken along lines 6-6 of FIGS. 3 and 4.

As is best seen in FIGS. 5 and 6 in combination with FIGS. 1 and 2, the bladder 54 is defined between an inner wall 62 and an outer wall 64. The inner wall 62 is adjacent the practitioners hand 11 and the outer wall abuts the surface of the birth canal 46, but extends outwardly from the birth canal to provide support for the practitioners forearm 12 when the practitioner's hand 11 is inserted through the birth canal.

The inner wall 62 of the bladder is preferably relatively stiff compared to the outer wall 64 so as to not unduly constrict the practitioner's forearm 12 while the outer wall is expanded against the wall of the birth canal 46 to widen the birth canal. Moreover, the bladder 54 does not extend over the palm of the practitioners hand 11 so as not to interfere with the flexibility of the palm and movement of the bones within the hand defining the metacarpus, which extend beyond the cuff portion 54 of the palm.

From the foregoing description, one skilled in the art can easily ascertain the essential characteristics of this invention, and without departing form the spirit and scope thereof, can make various changes and modifications of the invention to adapt it to various usages and conditions.

I claim:

1. A method of hand delivering an infant head first through a birth canal using a hand of a practitioner, comprising:
    covering the hand of the practitioner with a thin surgical glove;
    covering the hand of the practitioner with an expandable glove fitting over the surgical glove, the expandable glove having a trank;
    leaving fingers and a thumb of the practitioner free of the expandable glove so that the fingers and thumb project therefrom;
    inserting the hand of the practitioner covered by the surgical and expandable gloves into the birth canal;
    expanding the expandable glove by inflating an inflatable bladder installed within the trank of the expandable glove,
    gripping a head of the infant with the fingers and thumb of the practitioner while supporting the head of the infant with the palm of the hand of the practitioner, and
    withdrawing the infant through the birth canal.

2. The method of claim 1 employing the expandable glove covering the hand of the practitioner while exposing portions of the fingers and thumb of the practitioner; the expandable glove comprising:
    the trank having a wall covering at least a back of the hand of the practitioner;
    four finger sleeves and a thumb sleeve extending from the trank with each sleeve terminating at an open end, the sleeves each having a length such that the open ends terminate the sleeves in front of a proximal phalanx of each finger and thumb of the practitioner;
    a cuff extending from the trank and having a length sufficient to cover at least a portion of a forearm of the practitioner, and
    the inflatable bladder disposed at a location back from the finger and thumb sleeves and at least over the wall of the trank of the expandable glove so as to be adjacent to the back of the hand of the practitioner, the inflatable bladder being configured to be expandable away from the wall of the trank upon being inflated for widening the birth canal as the inflatable bladder inflates while the fingers and thumb of the practitioner hold the head of the infant being delivered, the inflatable bladder having a first end that is closed with the trank proximate the proximal phalanx of each finger and the proximal phalanx of the thumb and extending over the trank, the inflatable bladder being closed with the cuff at a location displaced substantially from the first end of the bladder.

3. The method of claim 1 including gripping the head of the infant with the surgical glove covering the fingers and thumb of the practitioner.

4. The method of claim 3 including inserting the hand of the practitioner into the surgical glove and then inserting the hand of the practitioner into the expandable glove prior to inserting the expandable glove into the birth canal.

5. The method of claim 1 wherein the inflatable bladder is inflated with compressed air introduced under control of the practitioner.

6. The method of claim 5 wherein the air is compressed by the other hand of the practitioner as the air is introduced into the inflatable ladder.

7. A method of hand delivering an infant head first through a birth canal using a hand of a practitioner, comprising:
    expanding the birth canal with an inflatable bladder in a trank of an expandable glove disposed over the back of one hand of the practitioner;
    leaving a palm, fingers and a thumb of the hand of the practitioner free of the inflatable bladder to allow flexibility of the palm, fingers and thumb;
    gripping a head of the infant with the fingers and thumb of the hand of the practitioner while supporting the head of the infant with the palm of the hand of the practitioner, and
    with the birth canal expanded by the inflatable bladder, withdrawing the infant through the birth canal.

8. The method of claim 7 wherein the fingers and thumb of the practitioner are exposed and free of the expandable glove.

9. The method of claim 8 wherein, the inflatable bladder covers and is expanded over a wrist and a forearm of the practitioner while being expanded in the trank over the back of the hand.

10. The method of claim 9 including gripping the head of the infant with a surgical glove covering the fingers and thumb of the practitioner.

11. The method of claim 10 including inserting the hand of the practitioner in the surgical glove and then inserting the hand of the practitioner into the expandable glove prior to inserting the expandable glove into the birth canal.

12. The method of claim 11 wherein the inflatable bladder is expanded by introducing air into the inflatable bladder.

13. The method of claim 12 wherein the air is compressed by the other hand of the practitioner as the air is introduced into the inflatable bladder.

14. A method of hand delivering an infant head first through a birth canal using a hand of a practitioner, comprising
    covering the hand of the practitioner with a thin surgical glove;
    covering the hand of the practitioner with an expandable glove fitting over the surgical glove, the expandable glove having a trank;
    leaving fingers and a thumb of the practitioner free of the expandable glove so that the fingers and thumb project therefrom;
    inserting the hand covered by the surgical and expandable gloves into the birth canal;
    expanding the expandable glove by inflating a bladder installed within the trank of the glove, gripping the head of the infant with the fingers and thumb while supporting a head with a palm of the hand of the practitioner, and withdrawing the infant through the birth canal.

\* \* \* \* \*